United States Patent
Savitski

(10) Patent No.: US 6,862,944 B2
(45) Date of Patent: Mar. 8, 2005

(54) NON-DESTRUCTIVE BUTT WELD INSPECTION METHOD

(75) Inventor: Alexander Savitski, Powell, OH (US)

(73) Assignee: Edison Welding Institute, Inc., Columbus, OH (US)

(*) Notice: Subject to any disclaimer, the term of this patent is extended or adjusted under 35 U.S.C. 154(b) by 80 days.

(21) Appl. No.: 10/250,741

(22) PCT Filed: Jan. 9, 2002

(86) PCT No.: PCT/US02/00425
§ 371 (c)(1),
(2), (4) Date: Jul. 9, 2003

(87) PCT Pub. No.: WO02/059566
PCT Pub. Date: Aug. 1, 2002

(65) Prior Publication Data
US 2004/0244509 A1 Dec. 9, 2004

Related U.S. Application Data
(60) Provisional application No. 60/260,492, filed on Jan. 9, 2001.

(51) Int. Cl.[7] .............................................. G01M 19/00
(52) U.S. Cl. ....................... 73/865.8; 73/150 A; 73/850
(58) Field of Search ............................... 73/865.8, 850, 73/150 A

(56) References Cited

U.S. PATENT DOCUMENTS

| | | | |
|---|---|---|---|
| 4,425,802 A | | 1/1984 | Sponseller |
| 4,475,963 A | * | 10/1984 | Takahashi et al. .......... 148/503 |
| 4,939,965 A | * | 7/1990 | Bircumshaw ................. 82/113 |
| 5,163,715 A | * | 11/1992 | Rickard et al. ................ 285/55 |
| 5,537,876 A | | 7/1996 | Davidson et al. |
| 5,738,268 A | | 4/1998 | VanderPol et al. |
| 5,874,146 A | | 2/1999 | Kagan et al. |

* cited by examiner

Primary Examiner—Hezron Williams
Assistant Examiner—Rodney Frank
(74) Attorney, Agent, or Firm—Gallagher & Dawsey Co., L.P.A.; Michael J. Gallagher; David J. Dawsey

(57) ABSTRACT

A non-destructive plastic butt weld inspection method in which the weld bead 42 is removed from an exterior surface of a weld zone region 44 of a butt weld and the weld zone region 44 is heated to a temperature sufficient to visualize the weld zone 44. After heating, defective joints are readily identified by the appearance of a bond line 40 in the weld zone 44 while satisfactory joints merely show the weld zone 44 with no evidence of a bond line 40. Surface irregularities such as ridges 46 and indentations 48 may also form in the weld zone during the heating step.

14 Claims, 3 Drawing Sheets

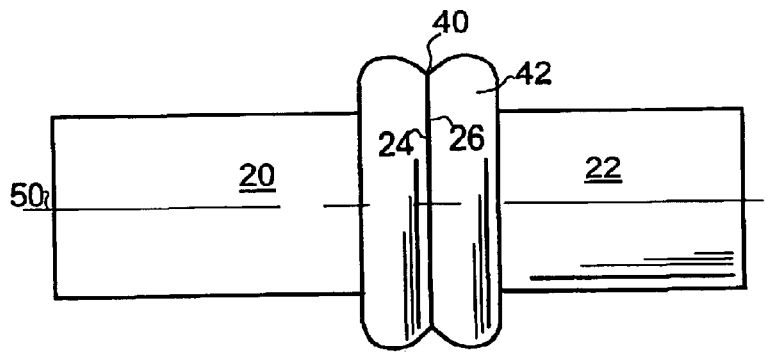
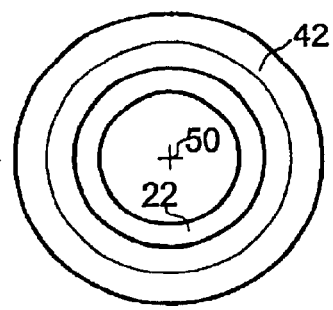
Fig. 3    Fig. 4
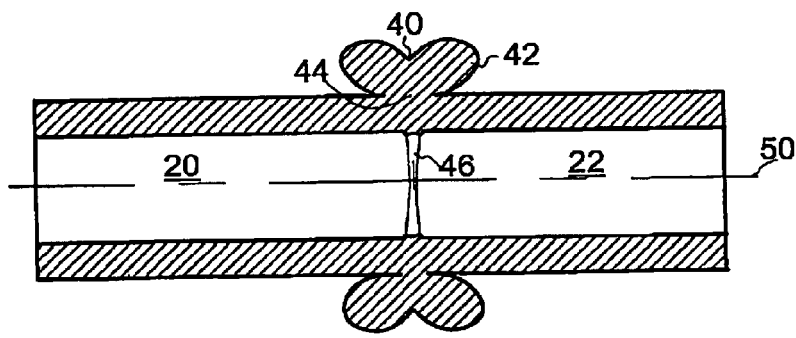
Fig. 5
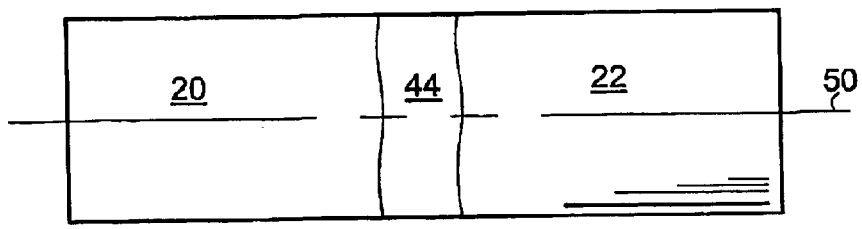
Fig. 6

NON-DESTRUCTIVE BUTT WELD INSPECTION METHOD

CROSS REFERENCE TO RELATED APPLICATION

This application claims the benefit of U.S. Provisional Application 60/260,492 filed on Jan. 9, 2001 all of which is incorporated by reference as if completely written herein.

BACKGROUND OF THE INVENTION

1. Field of the Invention

This invention pertains to inspection of plastic joints and more particularly to a non-destructive plastic butt-weld joint inspection method with emphasis on plastic pipe butt-weld joints.

2. Background of the Invention

Butt fusion processes have been successfully used for joining plastic pipes in water and gas-distribution systems for nearly three decades. As in many other critical applications, the quality of the joints greatly effects the overall operational safety of, the system. While mar failures of pipe butt fusion joints are infrequent, when they do occur, they can be dangerous and can result in significant loss.

Typically, butt joints fall because of weakened or incomplete fusion of the mating surfaces. This can occur as a result of several factors. For example, joint failure can occur as a result of insufficient pressure at portions of or over the entire periphery of the joint. Failure can occur due to premature solidification of the molten material in the weld zone due to weather conditions or due to an overextended open time. That is, the molten ends of the surfaces to be joined are allowed to cool excessively prior to the application of a bonding force. Failure can also occur due to contamination of the molten plastic Although ultrasonic instruments are available for nondestructive inspection of butt fusion joints, these devices are very expensive and their effectiveness and reliability for field inspection has not been fully ascertained. As a result, such instruments are not widely used. While it is possible to make cross-sectional cuts through the weld and make visual inspection using heating techniques to bring out joint defects, such destructive testing is useful only for training purposes. Clearly the destruction of the joint is counterproductive in a working system.

Presently, there is no simple and reliable method available for the non-destructive inspection of butt fusion joints. Typically the joints are assessed by visual inspection based on the size and shape of the weld bead. However, this method is subjective and can be misleading. For example, with an excessive, joint-formation heating time, most of the pipe material is displaced into the bead during the heating cycle rather than as a result of the joining (forging) pressure. Although visual inspection suggests an acceptable bead appearance, the joint is defective because of the excess loss of plastic in the joint region to the weld. As such, visual inspection simply cannot provide direct information as to the mechanical properties of a joint that result from the fusion process. The bead itself, plays an insignificant role in the joint strength and thus is not a reliable indicator of the underlying joint.

To overcome these problems, it is an object of the present invention to provide a non-destructive method of observing the quality of plastic butt joints.

Another object of the present invention is to provide an inexpensive method for the field testing of plastic joints such as plastic pipe joints.

A further object of the present invention is to provide a permanent record of the weld joint that can be stored for future reference.

Another object of the present invention is to enhance the accuracy of in-field weld inspection.

Yet another object of the present invention is to provide repeatable weld joint test results.

SUMMARY

To meet these and other objects of the current invention, a weld bead is removed from an exterior surface of a weld zone area of a butt weld, the weld zone region of the butt weld is heated to a temperature sufficient to render visible bonding in a heated weld zone region. After heating, the weld zone area rendered visible by the heating is inspected. The lack of a bond line in the weld zone region is indicative of a satisfactory joint while the presence of a bond line (an interface of the pieces being joined) in the weld zone region of the weld is indicative of a defective weld which should be rejected. Typically the weld bead can be removed by any appropriate means such as a cutting tool.

The weld zone region is heated by any convenient heating means such as radiant convention, or convective heating. Radiant heat can be supplied by an infrared lamp and convective heat by means of a hot-air gun. Heating of the weld zone region is continued to the softening point of the plastic that forms the butt weld.

For a permanent record of the weld, the weld zone region can be photographed after heating is complete. If a digital camera is used to produce a digital image, the image can be processed with image recognition software to detect the bond line. Alternatively laser-based pattern recognition systems may be used for bond line detection and recording.

The foregoing and other objects, features and advantages of the invention will become apparent from the following disclosure in which one or more preferred embodiments of the invention are described in detail and illustrated in the accompanying drawings. It is contemplated that variations in procedures, structural features and arrangement of parts may appear to a person skilled in the art without departing from the scope of or sacrificing any of the advantages of the invention.

BRIEF DESCRIPTION OF THE DRAWINGS

FIG. 3 is a plan view of the resulting butt weld of the two pipe sections shown in FIG. 2 after the hot plate has been removed and the ends brought in contact with each other under pressure.

FIG. 4 is a right end view of the butt weld joint shown in FIG. 3.

FIG. 5 is a cross-sectional view through the longitudinal axis of the butt weld joint of FIG. 3 illustrating the uniform intermixing of the ends of the two pipe sections in the weld zone region throughout the thickness of the pipe when the joint is formed under optimal conditions.

FIG. 6 is a plan view of the butt weld joint of FIG. 3 from which the weld bead has been removed and the weld zone region heated. Lack of the observation of a bond line in the weld zone region demonstrates the formation of a satisfactory weld (butt joint).

Figure 1:
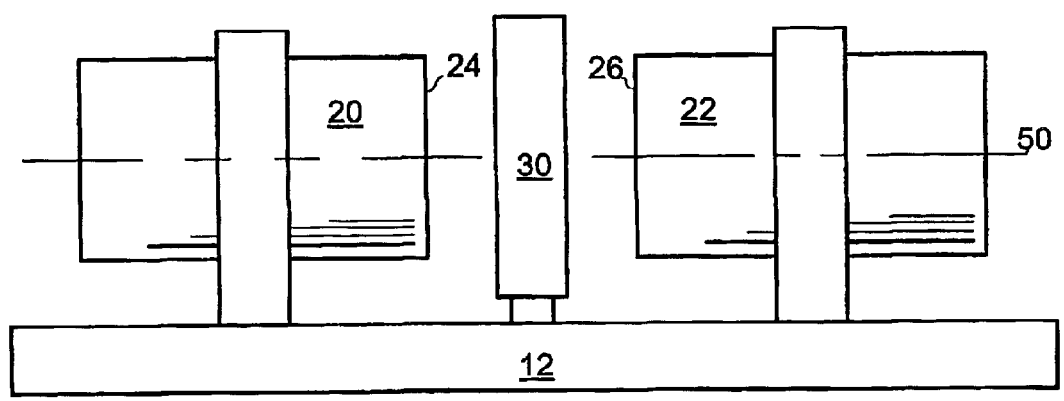
FIG. 1 is a plan view of two pipe sections placed in a axial aligning clamping device with a hot plate between the ends of the pipe sections.

In describing the preferred embodiment of the invention which is illustrated in the drawings, specific terminology is resorted to for the sake of clarity. However, it is not intended that the invention be limited to the specific terms so selected and ft is to be understood that each specific term includes all technical equivalents that operate in a similar manner to accomplish a similar purpose.

Although a preferred embodiment of the invention has been herein described, it is understood that various changes and modifications in the illustrated and described structure can be affected without departure from the basic principles that underlie the invention. Changes and modifications of this type are therefore deemed to be circumscribed by the spirit and scope of the invention, except as the same may be necessary modified by the appended claims or reasonable equivalents thereof.

DETAILED DESCRIPTION OF THE INVENTION AND BEST MODE FOR CARRYING OUT THE PREFERRED EMBODIMENT

Figure 2:
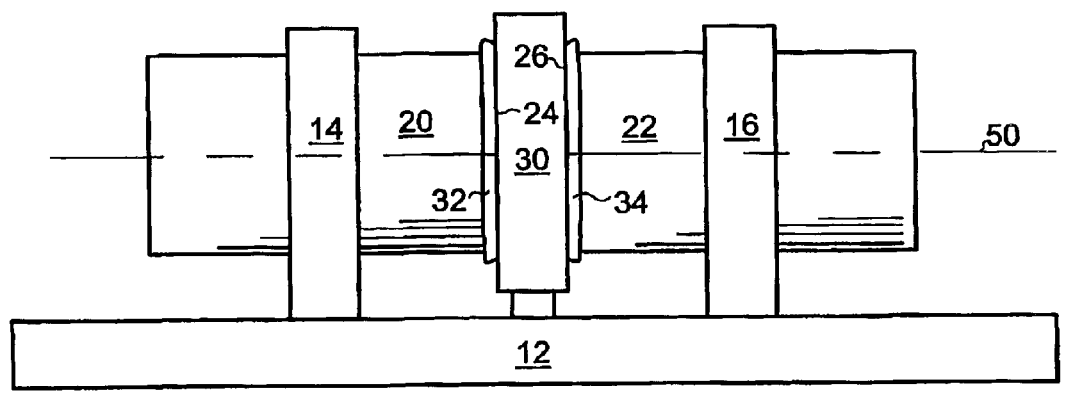
FIG. 2 is a plan view of the two pipe sections shown in FIG. 1 in which the ends of the pipe sections have been brought in contact with the hot plate and heated sufficiently to melt the end of the pipe sections.

In forming a typical butt weld as shown initially in FIGS. 1–2, sections 20, 22 of a thermo-plastic material such as poly-ethylene pipe are placed in a clamping device 12 and aligned with each other as noted by the common longitudinal center axis 50. The ends 24, 26 are planed until the ends are smooth and parallel. The ends 24, 26 are then brought in contact with a heated hot plate 30 (FIG. 2) until a uniform bead 32, 34 becomes visible around the perimeter of both ends 24, 26. The ends 24, 26 are retracted from the hot plate 30 which is removed. As seen in FIG. 3, the ends 24, 26 are quickly brought together with pressure to form a weld at the interface of the ends 24, 26 of each section 20, 22, respectively. Some of the molten thermoplastic material oozes from the interface of the ends 24, 26 of the two sections 20, 22 to form a weld bead 42. FIG. 4 is a right end view of FIG. 3 showing the weld bead 42. FIG. 5 is a cross section that illustrates the small weld bead 46 that is formed on the interior surface of the joined pipes 20, 22 as well as the weld zone region 44 in which the molten plastic from each section 20, 22 are thoroughly intermixed and fused to each other.

As shown especially in FIGS. 3 and 6, to practice the method of the current invention, the exterior weld bead 42 is removed, typically by cutting with a suitable cutting tool. At this point, the exterior surface of the joint is perfectly smooth and it is impossible to differentiate a good joint from a defective joint. After the exterior weld bead 42 has been completely removed, the weld zone region 44 is heated with a convenient heating device to a temperature sufficient to render visible the bonding between the sections 20, 22 of plastic material. After this secondary heating, the weld zone region 44 is visibly inspected and any weld exhibiting a bond line 40 is rejected. FIG. 6 illustrates a heated weld zone region 44 in which the butt-joint between the two sections 20, 22 was made under optimal conditions. It is to be noted that no bond line 40 between the two sections 20, 22 is visible nor are any surface distortions present. As seen in the cross section view of FIG. 5, the plastic from each section 20, 22 has fused and intermingled to produce a smooth continuous region throughout the weld region that is at least as thick as the thickness of the pipe.

The secondary heating step causes a relaxation of the material in the surface layer of the weld zone region 44 that eliminates the residual stress that developes when the melted polymer cools under pressure during the primary welding cycle. As a result of this material relaxation, the outline of the weld zone 44 becomes visible. As seen in FIG. 6, for a joint formed under optimal conditions, the material relaxation in the bond zone 44 produced by the secondary heating is merely a slight difference in texture over the entire bond zone 44 with no evidence of the initial interface (bond line) between the ends 24, 26 of sections 20, 22 apparent.

In cases where the butt-weld is not formed under optimal conditions, the intermolecular forces between the contacting ends 24, 26 do not fully develop as a result of incomplete fusion and intermixing of the molten material from each end 24, 26. When a secondary heating is made, relaxation of the macromolecules at the surface causes the material to pull back revealing a fusion or bond line 40.

Figure 7:
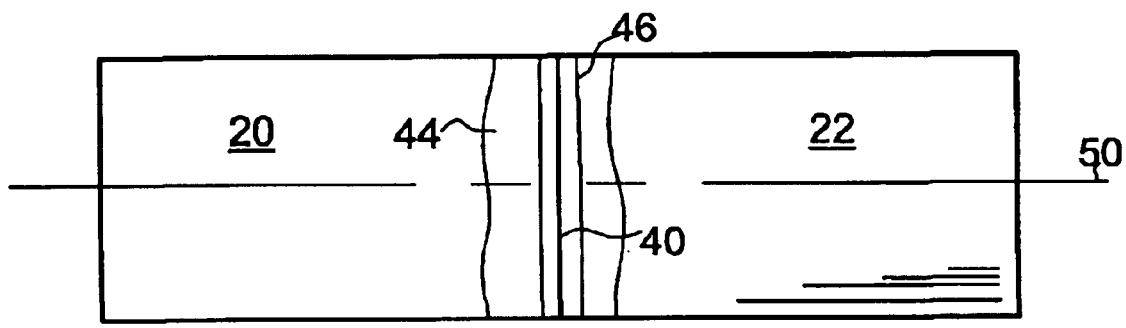
FIG. 7 is a plan view of a butt weld joint weld made with insufficient interfacial pressure in the initial joining step. The observation of the bond line and other deformities after the secondary heating step clearly shows the formation of a defective joint.
Figure 8:
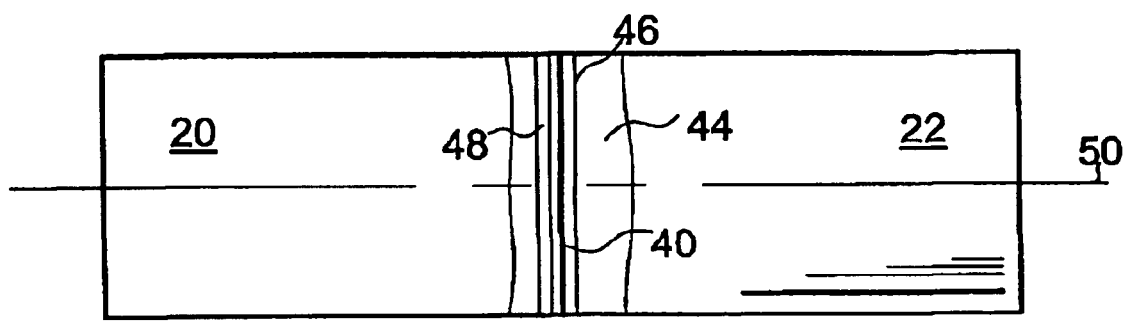
FIG. 8 is a plan view of the weld zone region after secondary heating. Illustrating the appearance of a bond line when the ends of the pieces are overheated prior to the initial joining step. The observation of the bond line after the secondary heating step dearly shows the formation of a defective joint.

FIG. 7 illustrates the presence of a bond line 40 between the two sections 20, 22 along with ridges 46 in the weld zone region 44 when the two sections 20, 22 are joined with insufficient interfacial pressure. FIG. 8 shows the presence of bond line 40 when the two sections 20, 22 are joined after heating the ends of the two sections 20, 22 to too high a temperature prior to the joining operation. In addition to the appearance of the defect indicating bond line 40, ridges 46 and valleys 48 may also develop on either side of the bond line 40 during the heating step. However, the observation of a bond line 40 is clear evidence of a defect weld. Butt weld failures are caused by weakened or incomplete fusion of the mating surfaces 24, 26 which give rise to the bond line 40. This can arise for a variety of reasons including insufficient pressure at portions or the entire interface of the joint, solidification of the material in the contact zone due to weather conditions, an over extended open time, contamination, and other factors. Regardless of the cause of the weak bond. Its presence can be readily identified by the appearance of the bond line 40 when the weld zone region 44 is rendered visible by a secondary heating step once the bond has been formed and allowed to cool.

Heating of the weld zone 44 for inspection may be carried out by any suitable heating method including radiant, conductive or convective heating. Suitable heating devices for carrying out the heating step include infrared lamps and hot-air guns. These devices are used to heat the plastic of the joined sections to the softening point of the plastic forming the butt weld. At this temperature, the bond between the two sections that have been joined becomes visible and defective welds can be easily identified by the appearance of the bond line 40 and other bond distortions. The visible bond can be photographed for a permanent record of the weld. Such photography can be carried out with a digital camera to produce a digital image which in turn may be processed with conventional image recognition software to detect the bond line. The visible bond can also be analyzed and recorded with a laser-based image recognition system such as commercially available from Edison Welding Institute (Columbus Ohio).

The method is useful for thermo-plastic materials such as polyethylene and polypropylene and is especially useful for the inspection of pipe butt welds such as those routinely found in fluid distribution systems such as water and gas distribution systems. The correlation between non-standard welding conditions and the appearance of a bond line and a corresponding reduction in joint mechanical properties was demonstrated experimentally of which the following examples are illustrative.

EXAMPLE I

Destructive Butt Weld Inspection Method—
Standard Welding Conditions

Eight-inch (20.3 cm) length pipe sections 20, 22 were cut from 4-inch (10.2 cm) diameter high density polyethylene (HDPE, Phillips Driscopipe 8100) pipe. Pipes were placed in the clamps of Widos Proweld 4 pipe welding unit 12 (Widos, Germany) and aligned. Pipe ends were planed with a facing unit until the ends were parallel and smooth. The facing unit was removed and the pipe ends were brought together and checked for final alignment and that no visible gaps existed between the ends 24, 26.

The clamps 14, 16 were retracted and a hot plate 30 at a temperature of 2300° C. (4460° F.) was placed between the pipes. The pipe ends 24, 26 were brought against the plate 30 firmly to ensure complete contact with an interface pressure of 0.15 MPa (21.8 psig). Completion of heating was evident by the formation of a uniform bead 32, 34 completely around the entire circumference of both ends 24, 26 at which time the pressure was dropped to a level sufficient to maintain the pipe ends 24, 26 in contact with the hot plate 30. At the end of the heating cycle, the ends 24, 26 of the pipe 20, 22 were retracted from the hot plate 30 and the hot plate 30 was removed. The molten ends 24, 26 were then quickly brought together and the interfacial pressure was raised to about 0.15 MPa and maintained until the weld was fully cooled.

The outer weld bead 42 was removed by grinding with 120 grit sandpaper. In the field, a debidding (bead 42 removal) operation is accomplished by using a conventional bead-cutting blade tool such as a McElroy debidding tool (McElroy Manufacturing, Tulsa, Okla.). Removal of the weld bead 42 has no significant effect on weld strength and is a technique commonly used in many countries outside of the United States. Even in the United States, the bead 42 is removed when plastic pipe is used as a steel pipe liner and pulled into previously installed pipe.

The weld zone 44 was then made visible by carrying out a secondary heating of the butt joint weld region 44. This heating can be done with any convenient heat source such as a radiant, convection or contact heat source. In the present instance, the weld zone 44 was visualized by directing the flow of hot air from a hot air gun on the sanded surface, keeping the nozzle approximately ⅜ inch (1 cm) from the surface. The surface was heated until the outline of the weld zone 44 became visible. The temperature setting for the hot air gun (Leister CH 6056 Hot Air Blower type Ghibli) was 480° F.–500° F. (249° C.–260° C.). FIG. 6 shows the exterior weld zone 44 of a joint made under optimal conditions after the secondary heating. The absence of the bond line or surface distortion shows good fusion between two sections 20, 22.

EXAMPLE II

Non-Destructive Butt Weld Inspection Method—
Insufficient Interfacial Pressure

The weld illustrated in FIG. 7 was prepared according to the method described above for Example I except that the interfacial pressure applied to the two pieces of pipe during the welding process was reduced by approximately 50%. The incompleteness of the weld is evident by the appearance of a bond line 40 between the two pipe segments 20, 22 along with slight ridges 46 on each side of the bond line 40.

EXAMPLE III

Destructive Butt Weld Inspection Method—
Excessive Heating Temperature

The weld illustrated in FIG. 8 was prepared according to the method described above for Example I except that the ends of the pipe were overheated during the initial welding process, that is, to a temperature of about 2800° C. As a result, the incompleteness of the weld is clearly evident by the appearance of the bond line 40 between the two pipe segments 20, 22 as well as ridges 46 and valleys (indentations) 48 on either side of the bond line 40.

It is possible that changes in configurations to other than those shown could be used but that which is shown is preferred and typical. Without departing from the spirit of this invention, various plastic configurations other than a pipe configuration may be used as well as a variety of heating methods to render the bond line visible.

It is therefore understood that although the present invention has been specifically disclosed with the preferred embodiment and examples, modifications to the design concerning sizing and shape will be apparent to those skilled in the art and such modifications and variations are considered to be equivalent to and within the scope of the disclosed invention and the appended claims.

I claim:

1. A method of non-destructive plastic butt weld inspection comprising:
   a) removing a weld bead from an exterior surface of a weld zone region of a butt weld;
   b) heating said weld zone region of said butt weld to a temperature sufficient to render visible bonding in said heated weld zone region;
   c) inspecting said weld zone region rendered visible by said heating; and
   d) rejecting said butt weld when a bond line is evident in said weld zone region.

2. The non-destructive method of plastic butt weld inspection according to claim 1 wherein said step of removing said weld bead from said weld zone region is carried out by cutting.

3. The non-destructive method of plastic butt weld inspection according to claim 1 wherein said heating step is a radiant heating step.

4. The non-destructive method of plastic butt weld inspection according to claim 3 wherein said radiant heating step is carried out with an infrared lamp.

5. The non-destructive method of plastic butt weld inspection according to claim 1 wherein said heating step is a conductive heating step.

6. The non-destructive method of plastic butt weld inspection according to claim 1 wherein said heating step is a convective heating step.

7. The non-destructive method of plastic butt weld inspection according to claim 6 wherein said convective heating step is carried out with a hot-air gun.

8. The non-destructive method of plastic butt weld inspection according to claim 1 wherein said heating step heats said weld zone region to a softening point of said plastic forming said butt weld.

9. The non-destructive-method of plastic butt weld inspection according to claim 1 further comprising the step of photographing said heated weld zone region rendered visible by said heating step.

10. The non-destructive method of plastic butt weld inspection according to claim 9 wherein said photographing step is carried out with a digital camera to produce a digital image.

11. The non-destructive method of plastic butt weld inspection according to claim 10 wherein said digital image is processed with image recognition software to detect said bond line.

12. The non-destructive method of plastic butt weld inspection according to claim 1 further comprising the step of detecting said bond line in said weld zone region rendered visible by said heating step with a laser-based image recognition system.

13. The non-destructive method of plastic butt weld inspection according to claim 1 wherein said butt weld is a plastic pipe butt weld.

14. The non-destructive method of plastic butt weld inspection according to claim 13 wherein said plastic pipe butt weld is a polyethylene plastic pipe butt weld.

* * * * *